United States Patent [19]

Whitcomb

[11] Patent Number: Plant 6,383

[45] Date of Patent: Nov. 8, 1988

[54] CRAPE MYRTLE

[75] Inventor: Carl E. Whitcomb, Stillwater, Okla.

[73] Assignee: Oklahoma State University, Stillwater, Okla.

[21] Appl. No.: 778,221

[22] Filed: Sep. 20, 1985

[51] Int. Cl.[4] ..... A01H 5/00

[52] U.S. Cl. ..... Plt./54

[58] Field of Search ..... Plt./54

*Primary Examiner*—Robert E. Bagwill

*Attorney, Agent, or Firm*—Head & Johnson

[57] ABSTRACT

A crape myrtle with a vigorous upright growth habit having up to 5 major stems and little if any secondary suckering at the base, large inflorescenses of wine-red flowers which discolor very little with age, and dark green leathery leaves that turn red-orange in the fall.

2 Drawing Sheets

BACKGROUND OF THE INVENTION

1. Field of the Invention:

The present invention relates to a new and distinct variety of cultivar of the ornamental shrub, *Lagerstroemia indica,* commonly known as crape myrtle.

2. Description of the Prior Art:

Most crape myrtle seedlings and cultivars flower early in the summer, set heavy seed crop and then flower sparsely the remainder of the growing season. Various attempts to develop improved varieties of the crape myrtle have been pursued commercially, including the issuance of several U.S. Plant patents. For example, U.S. Plant Pat. Nos. 4,182 through 4,185 disclose and claim a series of four new varieties of *Lagerstroemia indica* produced by crossing previously known unnumbered or unnamed seedlings. Each of these new varieties was characterized as having a weeping growth habit at full maturity. Also, U.S. Plant Pat. No. 4,189 discloses a new variety of crape myrtle produced by crossing seed parent SL blue (color 1-13) with pollen parent XX 224 blue star-shaped (color 1-13) and again, exhibiting a weeping growth habit at full maturity. In U.S. Plant Pat. No. 2,551, a dwarf habit hybrid of *Lagerstroemia indica* and *Lagerstroemia reginae* was disclosed and claimed.

It is generally known that ethylmethane sulfonate, EMS, is capable of producing mutant growth in plants. EMS frequently induces some degree of sterility in the plant mutant and the mutants often have thicker than normal leaves and variegated flowers, with an occasional flower that is a solid color among the predominantly variegated flowers. The new variety of crape myrtle of the present invention is felt to be a second generation of such a mutant.

SUMMARY OF THE INVENTION

I have discovered a new and distinct variety of crape myrtle, *Lagerstroemia indica,* which is characterized by a vigorous upright shrub with strong stems that may reach 2 to 3 m in height. The leaves of the plant are smaller and thicker than the species average and are dark green and red-orange in the fall. Inflorescences are 20 to 30 cm tall and 10 to 20 cm wide. Individual petals are dark wine-red. The new variety is cold hardy to −20° C. (4° F.) and is very resistant to drought and powdery mildew.

BRIEF DESCRIPTION OF THE DRAWINGS

A plant of the new variety is shown in full color in the accompanying photographs.

FIG. 1 is a view in full color showing the general form and arrangement of a typical bush or full plant.

FIG. 2 is a view in full color showing the flower head and leaves of a fully matured, flowered plant.

DESCRIPTION OF THE VARITY

The new variety of crape myrtle was selected from a second generation population seedling from parents that expressed mutant characteristics. An original lot of about 4,000 seeds collected from 16 seedling parents were treated with a 4 percent solution of ethylmethane sulfonate, EMS. Treated seeds from 32 plants that showed pronounced mutant characteristics (thick leathery leaves and variegated flowers) were collected. No control of pollination was attempted, herefore, the second generation seedlings were probably the result of the mutant parent and a normal parent. The seeds were planted in the greenhouse with no further chemical treatment. After the seeds germinated, powdery mildew was introduced from susceptible seedlings in large containers. Approximately 4,000 seedlings survived with little or no powdery mildew and were transplanted into the field. This new variety was discovered in and selected from this population.

Soft wood cuttings taken from the original parent have been successfully rooted (100 percent) in a medium of peat and perlite under intermittent mist. Subsequent cuttings taken from plants resulting from previous cuttings from the original parent have been similarly rooted. Growth and flowering of the rooted plants remain consistent with the parent. The plant does not reproduce true from seed.

A detailed description of the new variety of crape myrtle follows:

Parentage: The plant variety is selected from a second generation population of seedlings wherein one parent was derived from 4,000 common crape myrtle seeds, treated with ethylmethane sulfonate to induce mutations. The other parent is assumed to be a nonmutant in that no control of pollination was attempted. The thick leathery leaves, variegated flowers of one parent and long bloom time are all indications that the new variety is a mutant.

Growth: The plant is a vigorous, upright shrub or small tree with generally 3 to 5 stout major stems with few secondary branches or suckers from the base. The plants may reach 2 to 3 m in height with age.

Foliage: Leaves are smaller and thicker than species average, typically 4 to 5 cm wide and 5 to 9 cm long at full maturity. The leaves are dark green (Spinach green #0-960; color notations are from The Royal Horticulture Society Colour Chart) and red-orange in the fall. Fall color is variable depending on the season and growing condition.

Flowers: Inflorescences are 20 to 30 cm tall and 10 to 20 cm wide and are comprised of a plurality of flower heads varying typically from about 2 cm to 5 cm or larger. Individual petals are dark wine-red (Spiraea red #0-25; Royal Horticulture Society Colour) and discolor very little with age before falling. This is in direct contrast with both "Victor" and "Regal Red" which retain the old flowers which fade to an unattractive blue-purple to black before falling and distract from the remaining blooms.

The new variety begins flowering in late June and continues through early October in Central Oklahoma. After summer rains, inflorescences of most crape myrtle droop with the weight of the water. By contrast, due to the strength of the stem, the plant remains erect and attractive. The strong stems and few basal suckers provide for easy training as a tree form in hardiness zones 7b, 8, 9 and 10 (USDA). The large strongly upright inflorescenses appear much like a torch with a strong handle.

I claim:

1. A new and distinct variety of *Lagerstroemia indica* plant substantially as shown and described and particularly characterized by a vigorous upright growth habit, a plurality of major stems and little if any secondary suckering at the base, large inflorescenses of wine-red flower, Spiraea red #0-25, and dark green leathery leaves that turn red-orange in the fall.

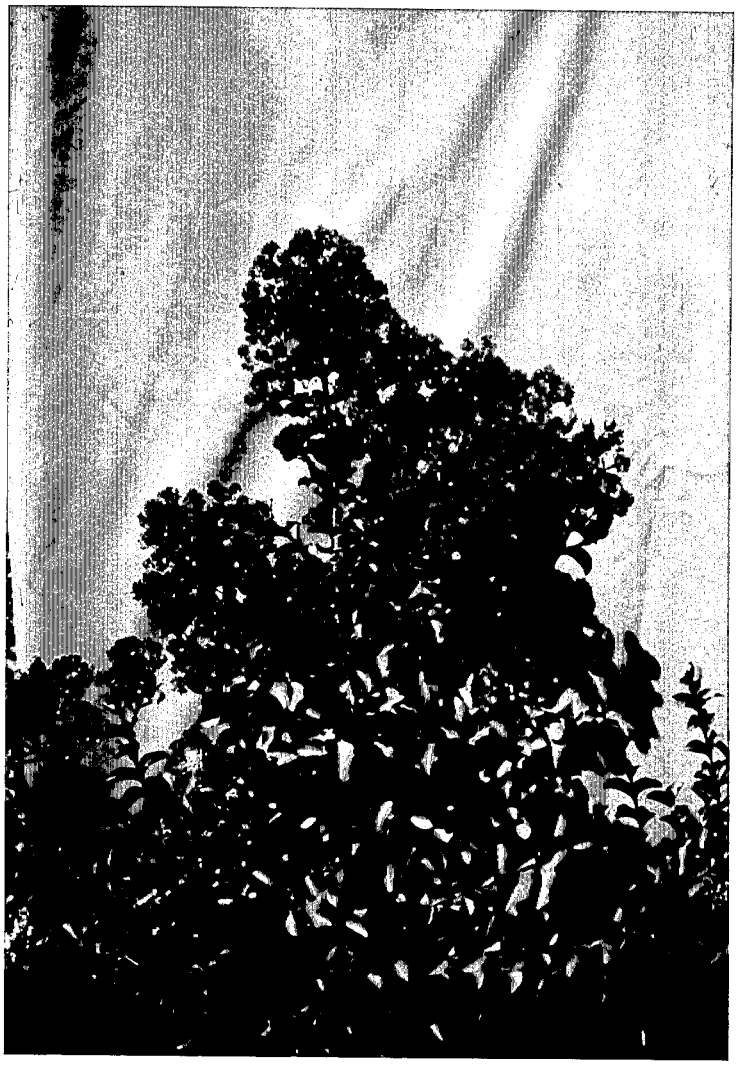

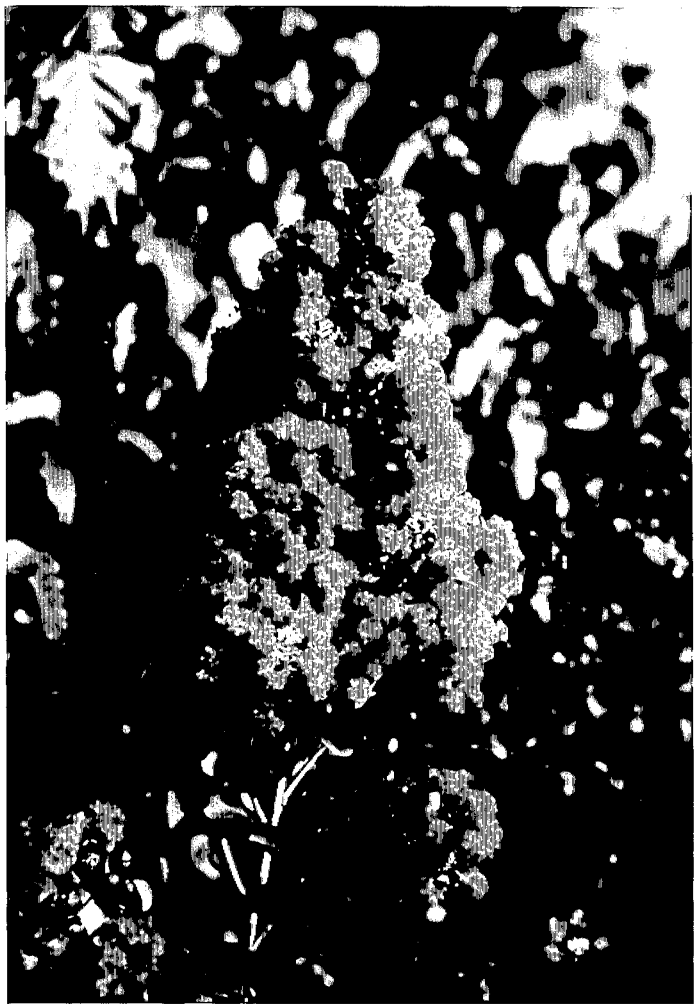

* * * * *